US011058875B1

(12) United States Patent
Zinner (10) Patent No.: US 11,058,875 B1
(45) Date of Patent: Jul. 13, 2021

(54) MOTOR FUNCTION IN SPINAL CORD INJURY PATIENTS VIA ELECTRICAL STIMULATION, AND ASSOCIATED SYSTEMS AND METHODS

(71) Applicant: Nevro Corp., Redwood City, CA (US)

(72) Inventor: Alex Zinner, Redwood City, CA (US)

(73) Assignee: Nevro Corp., Redwood City, CA (US)

( * ) Notice: Subject to any disclaimer, the term of this patent is extended or adjusted under 35 U.S.C. 154(b) by 118 days.

(21) Appl. No.: 16/575,797

(22) Filed: Sep. 19, 2019

Related U.S. Application Data

(60) Provisional application No. 62/733,554, filed on Sep. 19, 2018.

(51) Int. Cl.
*A61N 1/36* (2006.01)
*A61N 1/05* (2006.01)

(52) U.S. Cl.
CPC ....... *A61N 1/36003* (2013.01); *A61N 1/0553* (2013.01); *A61N 1/36062* (2017.08); *A61N 1/36157* (2013.01); *A61N 1/36175* (2013.01)

(58) Field of Classification Search
None
See application file for complete search history.

(56) References Cited

U.S. PATENT DOCUMENTS

| | | |
|---|---|---|
| 3,774,618 A | 11/1973 | Avery |
| 4,014,347 A | 3/1977 | Halleck et al. |
| 5,042,486 A | 8/1991 | Pfeiler et al. |
| 5,052,375 A | 10/1991 | Stark et al. |
| 5,078,140 A | 1/1992 | Kwoh |
| 5,211,165 A | 5/1993 | Dumoulin et al. |
| 5,257,636 A | 11/1993 | White |
| 5,325,873 A | 7/1994 | Hirschi et al. |
| 5,375,596 A | 12/1994 | Twiss et al. |
| 5,425,367 A | 6/1995 | Shapiro et al. |
| 5,643,330 A | 7/1997 | Holsheimer et al. |
| 5,727,553 A | 3/1998 | Saad |
| 5,871,487 A | 2/1999 | Warner et al. |
| 5,893,883 A | 4/1999 | Torgerson |

(Continued)

FOREIGN PATENT DOCUMENTS

| | | |
|---|---|---|
| EP | 2243510 | 10/2010 |
| JP | 2002090196 | 3/2002 |

*Primary Examiner* — Paula J Stice
(74) *Attorney, Agent, or Firm* — Perkins Coie LLP (57) ABSTRACT

Improving motor function in spinal cord injury patients (among others) via electrical stimulation, and associated systems and methods are disclosed. A representative method includes, in a patient having a spinal cord injury, improving the patient's gait response by delivering an electrical signal that includes repeating pulse packets delivered at a first frequency of from 2 Hz to 200 Hz. The electrical signal is delivered from an epidural location at the patient's spinal cord, and the individual pulse packets include a first period during which pulses are delivered at a first frequency of from 1 kHz to 5 kHz and a first pulse width of from 80 microseconds to 400 microseconds and a first amplitude from 0.1 mA to 20 mA, followed by a second period during which pulses are (a) not delivered, or (b) delivered at a second frequency higher than the first frequency, and/or a second pulse width shorter than the first pulse width, and/or a second amplitude less than the first amplitude.

21 Claims, 6 Drawing Sheets

(56) References Cited

U.S. PATENT DOCUMENTS

| | | | |
|---|---|---|---|
| 5,983,141 A | 11/1999 | Sluijter et al. | |
| 6,192,278 B1 | 2/2001 | Werner et al. | |
| 6,198,963 B1 | 3/2001 | Haim et al. | |
| 6,438,418 B1 | 8/2002 | Swerdlow et al. | |
| 6,440,090 B1 | 8/2002 | Schallhorn | |
| 6,474,341 B1 | 11/2002 | Hunter et al. | |
| 6,712,772 B2 | 3/2004 | Cohen et al. | |
| 6,757,561 B2 | 6/2004 | Rubin et al. | |
| 6,862,480 B2 | 3/2005 | Cohen et al. | |
| 6,871,090 B1 | 3/2005 | He et al. | |
| 6,875,571 B2 | 4/2005 | Crabtree et al. | |
| 6,950,707 B2 | 9/2005 | Whitehurst | |
| 7,020,523 B1 | 3/2006 | Lu et al. | |
| 7,082,333 B1 | 7/2006 | Bauhahn et al. | |
| 7,180,760 B2 | 2/2007 | Varrichio et al. | |
| 7,206,642 B2 | 4/2007 | Pardo et al. | |
| 7,212,867 B2 | 5/2007 | Van Venrooij et al. | |
| 7,236,834 B2 | 6/2007 | Christopherson et al. | |
| 7,241,283 B2 | 7/2007 | Putz | |
| 7,244,150 B1 | 7/2007 | Brase et al. | |
| 7,266,412 B2 | 9/2007 | Stypulkowski | |
| 7,313,440 B2 | 12/2007 | Miesel | |
| 7,329,262 B2 | 2/2008 | Gill | |
| 7,381,441 B2 | 6/2008 | Leung et al. | |
| 7,425,142 B1 | 9/2008 | Putz | |
| 7,606,622 B2 | 10/2009 | Reeve | |
| 7,702,379 B2 | 4/2010 | Avinash et al. | |
| 7,801,601 B2 | 9/2010 | Maschino et al. | |
| 7,826,901 B2 | 11/2010 | Lee et al. | |
| 7,856,277 B1 | 12/2010 | Thacker et al. | |
| 7,957,797 B2 | 6/2011 | Bourget et al. | |
| 7,957,809 B2 | 6/2011 | Bourget et al. | |
| 7,996,055 B2 | 8/2011 | Hauck et al. | |
| 8,016,776 B2 | 9/2011 | Bourget et al. | |
| 8,128,600 B2 | 3/2012 | Gill | |
| 8,131,357 B2 | 3/2012 | Bradley et al. | |
| 8,170,675 B2 | 5/2012 | Alataris et al. | |
| 8,197,494 B2 | 6/2012 | Jaggi et al. | |
| 8,209,021 B2 | 6/2012 | Alataris et al. | |
| 8,209,028 B2 | 6/2012 | Skelton et al. | |
| 8,355,791 B2 | 1/2013 | Moffitt | |
| 8,423,147 B2 | 4/2013 | Alataris et al. | |
| 8,428,748 B2 | 4/2013 | Alataris et al. | |
| 2003/0135241 A1 | 7/2003 | Leonard et al. | |
| 2003/0199952 A1 | 10/2003 | Stolz et al. | |
| 2003/0208244 A1 | 11/2003 | Stein et al. | |
| 2004/0176812 A1 | 9/2004 | Knudson et al. | |
| 2004/0186544 A1 | 9/2004 | King | |
| 2004/0199214 A1 | 10/2004 | Merfeld et al. | |
| 2004/0210290 A1 | 10/2004 | Omar-Pasha | |
| 2005/0004417 A1 | 1/2005 | Nelson et al. | |
| 2005/0004638 A1 | 1/2005 | Cross | |
| 2005/0038489 A1 | 2/2005 | Grill | |
| 2005/0049664 A1 | 3/2005 | Harris et al. | |
| 2006/0089697 A1 | 4/2006 | Cross et al. | |
| 2007/0066995 A1 | 3/2007 | Strother et al. | |
| 2007/0142874 A1 | 6/2007 | John | |
| 2007/0162088 A1 | 7/2007 | Chen et al. | |
| 2008/0140153 A1 | 6/2008 | Burdulis | |
| 2009/0281596 A1 | 11/2009 | King | |
| 2010/0331920 A1 | 12/2010 | DiGiore et al. | |
| 2011/0301679 A1 | 12/2011 | Rezai | |
| 2013/0035740 A1 | 2/2013 | Sharma et al. | |
| 2013/0066411 A1 | 3/2013 | Thacker et al. | |
| 2014/0067016 A1 | 3/2014 | Kaula | |
| 2014/0081350 A1 | 3/2014 | Zhu | |
| 2014/0180361 A1* | 6/2014 | Burdick | A61N 1/36103 607/49 |
| 2014/0343622 A1 | 11/2014 | Alataris | |
| 2015/0151125 A1 | 6/2015 | Zhu | |
| 2015/0165209 A1 | 6/2015 | Grandhe | |
| 2015/0321000 A1 | 11/2015 | Rosenbluth | |
| 2016/0271392 A1* | 9/2016 | Vallejo | A61N 1/36196 |
| 2017/0189686 A1* | 7/2017 | Steinke | A61N 1/0551 |
| 2018/0345022 A1* | 12/2018 | Steinke | A61N 1/36125 |
| 2019/0022382 A1* | 1/2019 | Gerasimenko | A61N 1/36003 |
| 2019/0232064 A1 | 8/2019 | Parker | |

* cited by examiner

MOTOR FUNCTION IN SPINAL CORD INJURY PATIENTS VIA ELECTRICAL STIMULATION, AND ASSOCIATED SYSTEMS AND METHODS

CROSS-REFERENCE TO RELATED APPLICATION

The present application claims priority to U.S. Provisional Application No. 62/733,554, filed on Sep. 19, 2018, and incorporated herein by reference.

TECHNICAL FIELD

The present technology is directed generally to improving motor function in spinal cord injury patients (among others) via electrical stimulation, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (e.g., contacts) spaced apart from each other at the distal end of the lead body. The conductive rings operate as individual electrodes and, in many cases, the SCS leads are implanted percutaneously through a needle inserted into the epidural space, with or without the assistance of a stylet. In other systems, the electrodes are carried by a paddle that is implanted via a laminotomy.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain.

Aspects of the present technology are directed to methods and systems improving motor function in spinal cord injury patients (and/or other patients) via electrical signals applied to the spinal cord.

DETAILED DESCRIPTION

Definitions of selected terms are provided under Heading 1.0 ("Definitions"). General aspects of the anatomical and physiological environment in which the disclosed technology operates are described below under Heading 2.0 ("Introduction"). Representative treatment systems and their characteristics are described under Heading 3.0 ("System Characteristics") with reference to FIGS. 1A, 1B and 2. Representative methods for treating patients are described under Heading 4.0 ("Representative Methods for Treating Patient Motor Function") with reference to FIGS. 3A-4. Representative examples are described under Heading 5.0 ("Representative Examples").

1.0 Definitions

Unless otherwise stated, the terms "about" and "approximately" refer to values within 10% of a stated value.

As used herein, and unless otherwise noted, the terms "modulate," "modulation," "stimulate," and "stimulation" refer generally to signals that have an inhibitory, excitatory, and/or other effect on a target neural population. Accordingly, a spinal cord "stimulator" can have an inhibitory effect on certain neural populations.

2.0 Introduction

The present technology is directed generally to spinal cord modulation and associated systems and methods for treating motor dysfunctions in patients. In some embodiments, representative techniques include applying a therapy signal that includes packets of pulses having therapy signal parameters selected to improve the patients' motor functioning. For example, the therapy signal can improve the gait of a patient suffering the effects of a spinal cord injury. The packets can each include two (or more) periods, and can be delivered at a frequency of from 2 Hz to 200 Hz. During the first period of an individual packet, the electrical therapy signal is delivered at a frequency of from 1 kHz to 5 kHz. During the second period, the electrical therapy signal can be halted, or it can be delivered with different signal parameters. For example, during the second period, the therapy signal can be delivered at a frequency of from about 1.2 kHz to 100 kHz. In any of the foregoing embodiments, the portion of the therapy signal delivered during the first period is expected to produce a beneficial impact on the patient's motor functioning. More specifically, in at least some embodiments, the portion of the therapy signal delivered during the first period has been observed to improve the patient's gait during physical therapy and/or other ambulatory tasks, despite the patient's disabilities resulting from a spinal cord injury. During the second period, the therapy signal can be, if desired, targeted to addressing the patient's pain and accordingly, can have different parameters than during the first period. The spinal cord injury can result from any of a number of causes, including trauma (e.g., an accident) and/or degenerative nerve disease.

Specific details of some embodiments of the present technology are described below with reference to methods for modulating one or more target neural populations within the patient's spinal cord and/or spinal cord region, and associated implantable structures for providing the modulation. Some embodiments can have configurations, components and/or procedures different than those described herein, and other embodiments may eliminate particular components or procedures. A person of ordinary skill in the relevant art, therefore, will understand that the present technology may include some embodiments with additional elements, and/or may include some embodiments without several of the features shown and described below with reference to FIGS. 1A-4.

3.0 System Characteristics

Figure 1A:
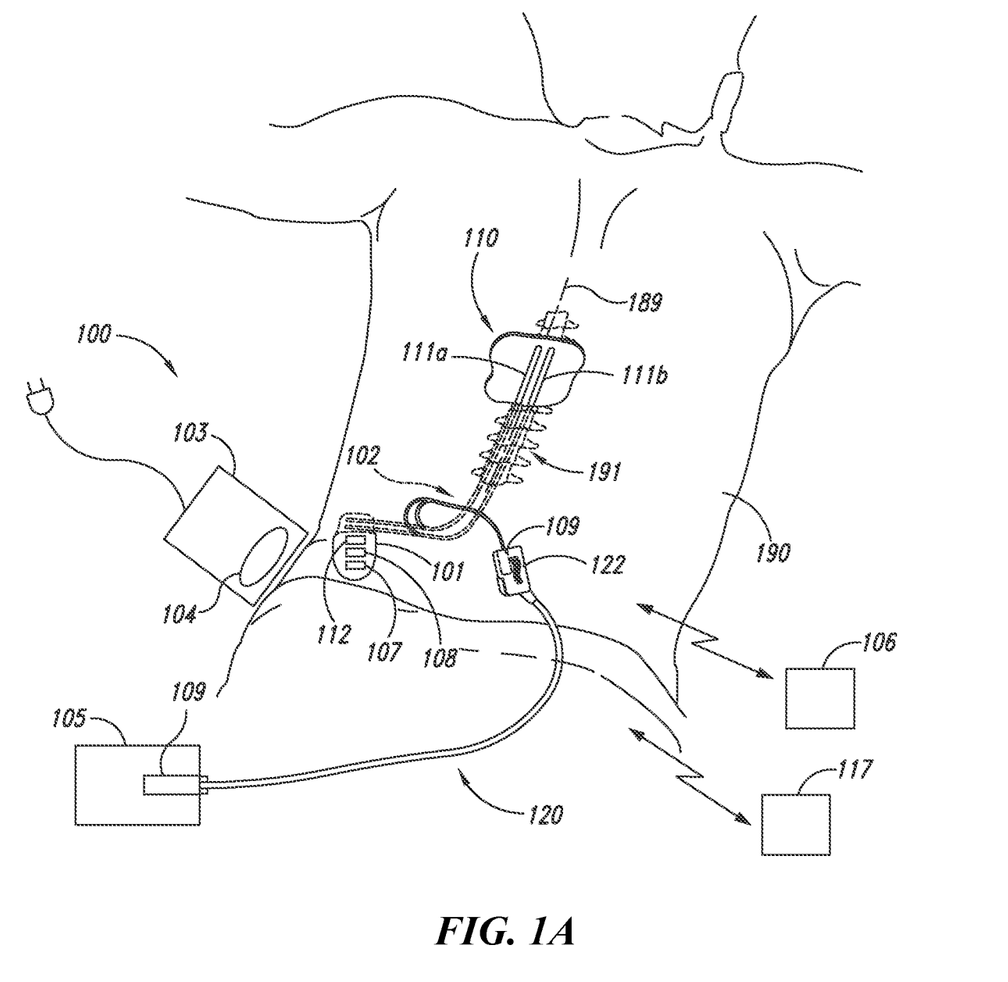
FIG. 1A is a partially schematic illustration of an implantable spinal cord modulation system positioned at a patient's spine to deliver therapeutic signals in accordance with some embodiments of the present technology.

FIG. 1A schematically illustrates a representative patient therapy system 100 for treating a patient's motor and/or other functioning, arranged relative to the general anatomy of the patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms signal delivery device, signal delivery element, lead, and/or lead body include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, incorporated herein by reference in its entirety. For example, paddles may be more suitable for patients with spinal cord injuries that result in scarring or other tissue damage that impedes cylindrical leads.

In some embodiments, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In some embodiments, the leads 111 may be implanted at a vertebral level ranging from, for example, about T4 to about T12. In some embodiments, one or more signal delivery devices can be implanted at other vertebral levels, e.g., as disclosed in U.S. Pat. No. 9,327,121, which is incorporated herein by reference in its entirety.

The signal generator 101 can transmit signals (e.g., electrical signals) to the signal delivery elements 110 that excite and/or suppress target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described in the materials incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings. For example, the signal generator can include some components that are implanted (e.g., a circuit that directs signals to the signal delivery device 110), and some that are not (e.g., a power source). The computer-executable instructions can be contained on one or more media that are implanted within the patient and/or positioned external to the patient, depending on the embodiment.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. For example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, which is incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patient's remote or remote device, etc.).

Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept inputs corresponding to pain relief, motor functioning and/or other variables, such as medication use. Accordingly, more generally, the present technology includes receiving patient feedback, via a sensor, that is indicative of, or otherwise corresponds to, the patient's response to the signal. Feedback includes, but is not limited to, motor, sensory, and verbal feedback. In response to the patient feedback, one or more signal parameters can be adjusted, such as frequency, pulse width, amplitude or delivery location.

Figure 1B:
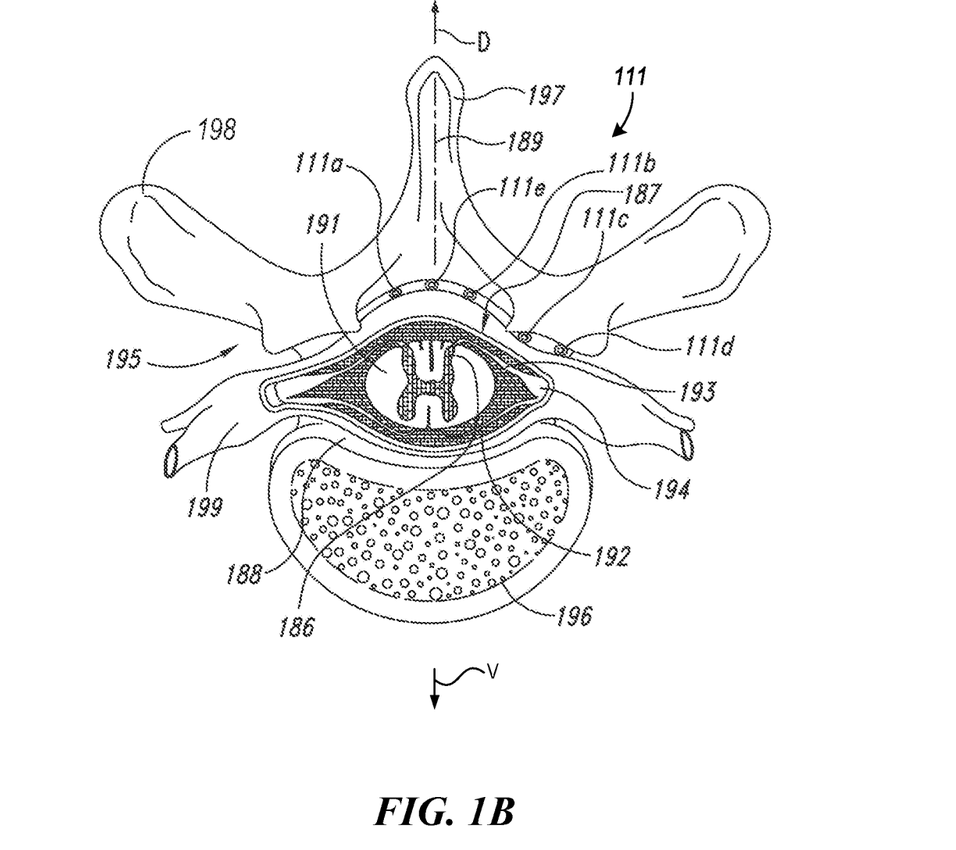
FIG. 1B is a partially schematic, cross-sectional illustration of a patient's spine, illustrating representative locations for implanted lead bodies in accordance with some embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated leads however, leads 111 can be paddle leads. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry region 187, and communicate with dorsal horn neurons located at the dorsal horn 186. In some embodiments, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In some embodiments, a lead or pairs of leads can be positioned at other locations, e.g., toward the outer edge of the dorsal root entry portion 187 as shown by a third lead 111c, or at the dorsal root ganglia 194, as shown by a fourth lead 111d, or approximately at the spinal cord midline 189, as shown by a fifth lead 111e.

In some embodiments the devices and systems of the present technology include features other than those described herein. For example, one lead 111 to six leads 111 can be positioned generally end-to-end at or near the patient's midline M and span vertebral levels from about T4 to about T12. In some embodiments, two, three, or four leads 111 are positioned end-to-end at or near the patient's midline from T4 to T12. In some embodiments, the leads 111 and/or other signal delivery devices can have locations other than those expressly shown herein. For example, one or more signal delivery devices can be positioned at the ventral side of the spinal cord 191 (e.g., to address gait and/or other motor functioning) and, optionally, one or more signal delivery devices can be positioned at the dorsal side of the spinal cord 191 (e.g., to address chronic and/or other pain). In addition, the devices and systems of the present technology can include more than one internal stimulator and/or more than one external stimulator that can be configured for wireless stimulation, such as by using electromagnetic waves.

Several aspects of the technology are embodied in computing devices, e.g., programmed/programmable pulse generators, controllers and/or other devices. The computing devices on/in which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In some embodiments, the computer readable media are tangible media. In some embodiments, the data structures and message structures may be stored or transmitted via an intangible data transmission medium, such as a signal on a communications link. Various suitable communications links may be used, including but not limited to a local area network and/or a wide-area network.

Figure 2:
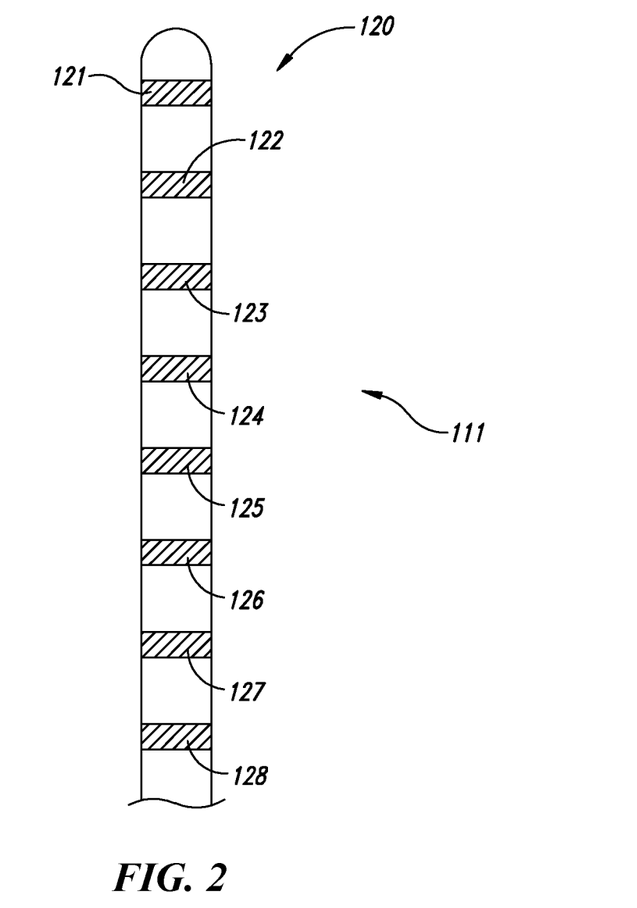
FIG. 2 is a schematic illustration of a representative lead body suitable for providing modulation to a patient in accordance with several embodiments of the present technology.

FIG. 2 is a partially schematic illustration of a representative lead body 111 that may be used to apply modulation to a patient in accordance with any of the foregoing embodiments. In general, the lead body 111 includes a multitude of electrodes or contacts 120. When the lead body 111 has a circular cross-sectional shape, as shown in FIG. 2, the contacts 120 can have a generally ring-type shape and can be spaced apart axially along the length of the lead body 111. In a particular embodiment, the lead body 111 can include eight contacts 120, identified individually as first, second, third . . . eighth contacts 121, 122, 123 . . . 128. In general, one or more of the contacts 120 are used to provide signals, and another one or more of the contacts 120 provide a signal return path. Accordingly, the lead body 111 can be used to deliver monopolar modulation (e.g., if the return contact is spaced apart significantly from the delivery contact), or bipolar modulation (e.g., if the return contact is positioned close to the delivery contact and in particular, at the same target neural population as the delivery contact). In still further embodiments, the pulse generator 101 (FIG. 1A) can operate as a return contact for monopolar modulation.

4.0 Representative Methods for Treating Patient Motor Functions

Figure 3A:
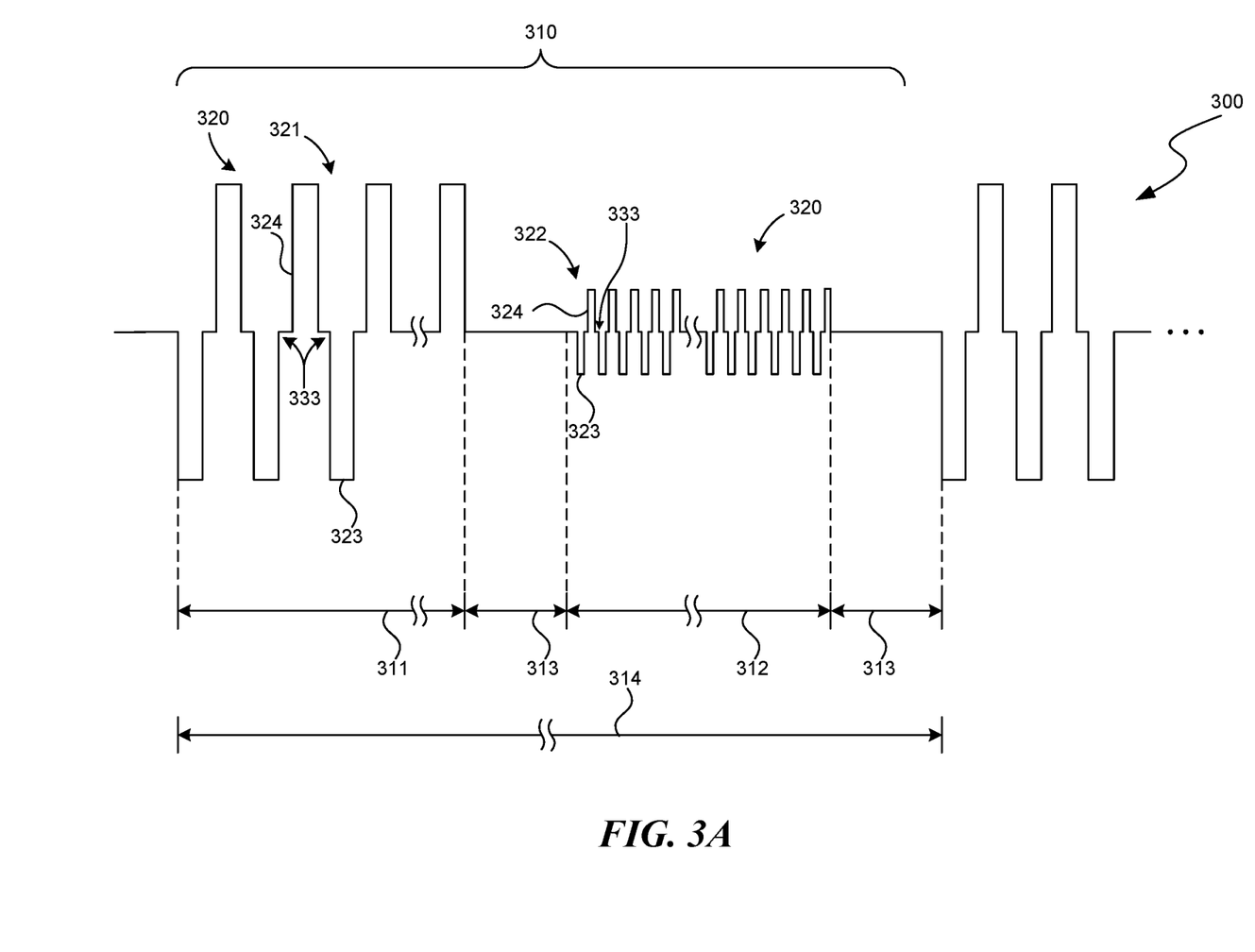
FIGS. 3A and 3B illustrate representative waveforms for delivering therapy to patients in accordance with embodiments of the present technology.

FIG. 3A is a partially schematic illustration of a representative therapy signal 300 used to deliver therapy in accordance with embodiments of the present technology. The therapy signal 300 can be made up of multiple packets 310 that are delivered to the patient on a repeating basis. Each packet can include a first period 311 followed by a second period 312, optionally with an inter-period interval 313 between the first and second periods 311, 312, and/or after the second period 312 (or before the first period 311). Accordingly, the overall packet 310 can have a packet period 314 that is the sum of the first period 311, the second period 312, and any inter-period intervals 313. The frequency with which the packet 310 is repeated (e.g., the signal frequency or the packet frequency) corresponds to the inverse of the packet period 314.

The first period 311 and/or the second period 312 can each include multiple pulses 320. Accordingly, as shown in FIG. 3A, the first period 311 can include first pulses 321, which in turn include cathodic pulses 323 and anodic pulses 324, optionally separated by inter-pulse intervals 333. During the second period 312, the electrical signal can be stopped, in some embodiments. In other embodiments, the second period 312 includes second pulses 322, which also include anodic pulses 323 and cathodic pulses 324, optionally separated by inter-pulse intervals 333. The second period 312 can occur before or after the first period 311.

Figure 3B:
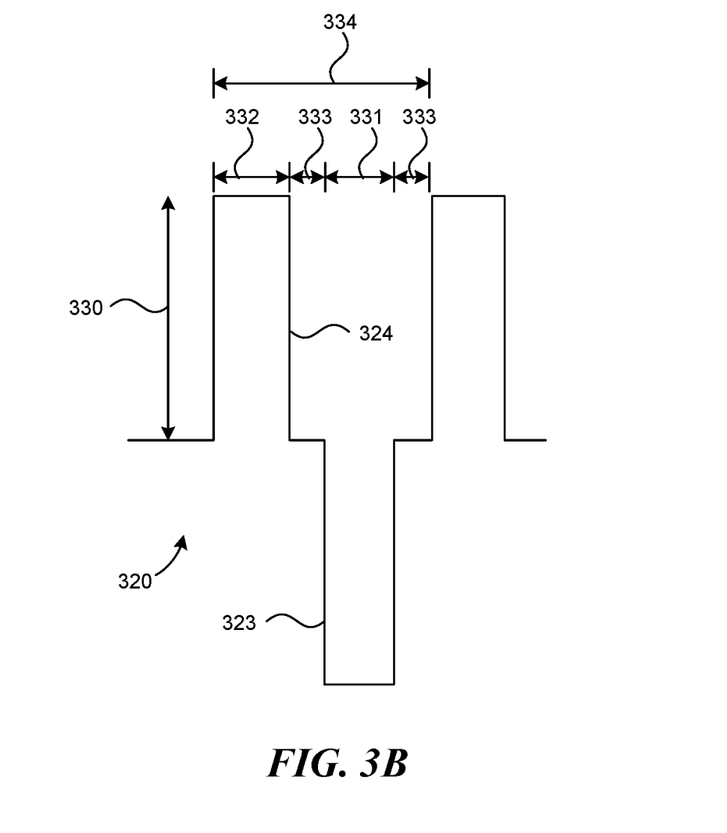

FIG. 3B is an enlarged illustration of several representative pulses 320, which can correspond to the first pulses 321 and/or the second pulses 322 shown in FIG. 3A. The cathodic pulses 323 can be characterized by a cathodic pulse width 331, and the anodic pulses 324 can be characterized by an anodic pulse width 332. Individual pulses can be separated by an inter-pulse interval 333. A corresponding pulse period 334 includes the cathodic pulse width 331, the anodic pulse width 332, and any inter-pulse intervals 333. The frequency of the pulses is the inverse of the pulse period 334.

Referring to FIGS. 3A and 3B together, the overall signal 300 can include multiple packets 310 delivered at a frequency (e.g., a packet frequency) that is the inverse of the packet period 314. The first pulses 321 are delivered during the first period 311 and, optionally, second pulses 322 are delivered during the second period 312. The amplitude 330, cathodic pulse width 331, anodic pulse width 332, inter-pulse interval 333, and pulse period 334 can be different for the first pulses 321 than for the second pulses 322.

In a representative example, a patient with a spinal cord crush injury at T12 received a therapy signal 300 with the first pulses 321 delivered at a frequency of 3 kHz, a cathodic pulse width 331 of 140 microseconds, and an anodic pulse width 332 of 140 microseconds. The inter-pulse interval 333 was 20 microseconds. The amplitude of the first pulses 321 was 5 mA, and the first period 311 was 3 milliseconds. The signal was delivered via electrodes carried by two epidural leads placed approximately the midline of vertebral level T12, on the dorsal side of the spinal cord.

During the second period 312, the patient received second pulses 322 at a frequency of 10 kHz, with a cathodic pulse width 331 of 30 microseconds, an anodic pulse width 332 of 30 microseconds, and an inter-pulse interval 333 before and after each anodic pulse 323 of 20 microseconds. The inter-period intervals 313 were 300 microseconds. The first period 311 was set at 3 milliseconds, and the second period 312 was set at 27 milliseconds, for a packet period 314 of 30 milliseconds. The packet frequency (the inverse of the packet period 314) was 33 Hz.

The result of the foregoing treatment regimen was that the patient's gait was significantly improved. In particular, the patient's gait was less jerky and/or smoother compared to the gait after conventional therapy techniques, or the absence of therapy. In addition, the patient reported a sensation of mild tingling, akin to putting legs in a warm bath, which aided with proprioception. Still further, the patient reported improved urological sensation (e.g., the ability to detect a full bladder). Contrasting conventional techniques include applying a therapy signal at a low frequency of from about 5 Hz to about 200 Hz, in a continuous manner. Another conventional therapy technique includes supplementing the low frequency therapy with a 10 kHz signal during the otherwise quiescent period between the low frequency pulses. As noted above, the patient experienced an improved outcome compared with both of the foregoing conventional techniques, both from a motor perspective and from a sensory perspective It is expected that, as a result of the second pulses delivered to the patient, the patient will experience pain relief without paresthesia, as has been demonstrated by Nevro Corp. via its HF10™ therapy, disclosed in U.S. Pat. No. 8,712,533, which is incorporated herein by reference. However, it is also believed that the patient can experience an improvement in motor function (e.g., gait performance)

without the signal being applied during the second period 312. For example, if the patient is not suffering from pain, the patient can forego receiving the therapy signal during the second period 312. Accordingly, the second period 312 can include pulses, for example, to alleviate the patient's pain (if the patient has pain), or can be devoid of pulses (for example, if the patient has no pain). In some embodiments, the patient and/or practitioner can activate signal delivery during the second period on an as-needed or as-desired basis.

The signal parameters described above can have values other than the specific values described above. For example, the amplitude of the first pulses can have a value in a range of from about 0.5 mA to about 20 mA. The first pulses can be provided at a frequency of from about 1 kHz to about 5 kHz. The first pulses can include biphasic, square-wave, symmetric anodic and cathodic pulses 323, 324, as shown in FIG. 3A, or can have other pulse shapes that are charge-balanced (as shown in FIG. 3A), or not charge balanced. In general, it is expected that charge-balanced pulses will reduce the likelihood for corrosion and/or other detrimental effects on the electrodes or contacts that are used to deliver the pulses. The pulse widths of the first pulses can be in a range of about 80 microseconds to about 400 microseconds. In particular embodiments, the first pulses can have a pulse width in a range of from about 80 microseconds to about 200 microseconds, or from about 100 microseconds to about 140 microseconds.

Similarly, the second pulses 322 can have parameter values other than those specifically described above. For example, the second pulses can be delivered at a frequency in a frequency range between about 1.2 kHz and about 100 kHz; or between about 1.5 kHz and about 100 kHz, or between about 1.5 kHz and about 50 kHz; or between about 3 kHz and about 20 kHz; or between about 3 kHz and about 15 kHz; or between about 5 kHz and about 15 kHz; or at frequencies of about 5 kHz, about 6 kHz, about 7 kHz, about 8 kHz, about 9 kHz, about 10 kHz, about 11 kHz, or about 12 kHz. In general (but not necessarily in all cases), the second pulses are delivered at a higher frequency than the first pulses.

The second pulses can have amplitudes within amplitude ranges of: about 0.1 mA to about 20 mA; about 0.5 mA to about 10 mA; about 0.5 mA to about 7 mA; about 0.5 mA to about 5 mA; about 0.5 mA to about 4 mA; or about 0.5 mA to about 2.5 mA.

In some embodiments, the second pulses can have a pulse width in a pulse width range of from about 5 microseconds to about 400 microseconds, for a single anodic or cathodic phase, or from about 5 microseconds to about 400 microseconds; or from about 8 microseconds to about 400 microseconds, or from about 5 microseconds to about 200 microseconds, or from about 5 microseconds to about 166 microseconds; or from about 25 microseconds to about 166 microseconds; or from about 25 microseconds to about 100 microseconds; or from about 30 microseconds to about 100 microseconds; or from about 33 microseconds to about 100 microseconds; or from about 50 microseconds to about 166 microseconds. In general, the second pulses will have a narrower pulse width than the first pulses.

As indicated above, the second pulses 322 (if present) can be delivered at a higher frequency than the first pulses 321. In addition to, or in lieu of the foregoing feature, the second pulses 322, if delivered, can be delivered at a lower amplitude than the first pulses 321. The combination of a lower amplitude and higher frequency is expected to produce the paresthesia-free pain relief described in U.S. Pat. No. 8,712,533, previously incorporated herein by reference. Conversely, the lower frequency, higher amplitude first pulses 321 are expected to produce the gait improvement effect described above. Furthermore, for patients suffering from spinal cord injury and, as a result, having increased sensory thresholds, the amplitude of the first pulses 321 can be increased compared to normal patients. It is expected that the increased amplitude can be a factor in producing the observed gait improvement.

The specific example described above was described in the context of a patient suffering from spinal cord injury, and addressed the patient's gait deficiencies. In other embodiments, similar techniques can be used to treat patients having indications other than spinal cord injury, and can produce motor system benefits other than improved gait. For example, while the foregoing therapy may be applied to the thoracic portion of the patient's spinal cord to address lower limb disorders (e.g., at a vertebral level from T8-T12), in other embodiments, the signal can be applied to other vertebral levels to address other indications, for example, upper extremity indications, head and neck indications, and/or others. Suitable locations range from C1 to S5.

Figure 4:
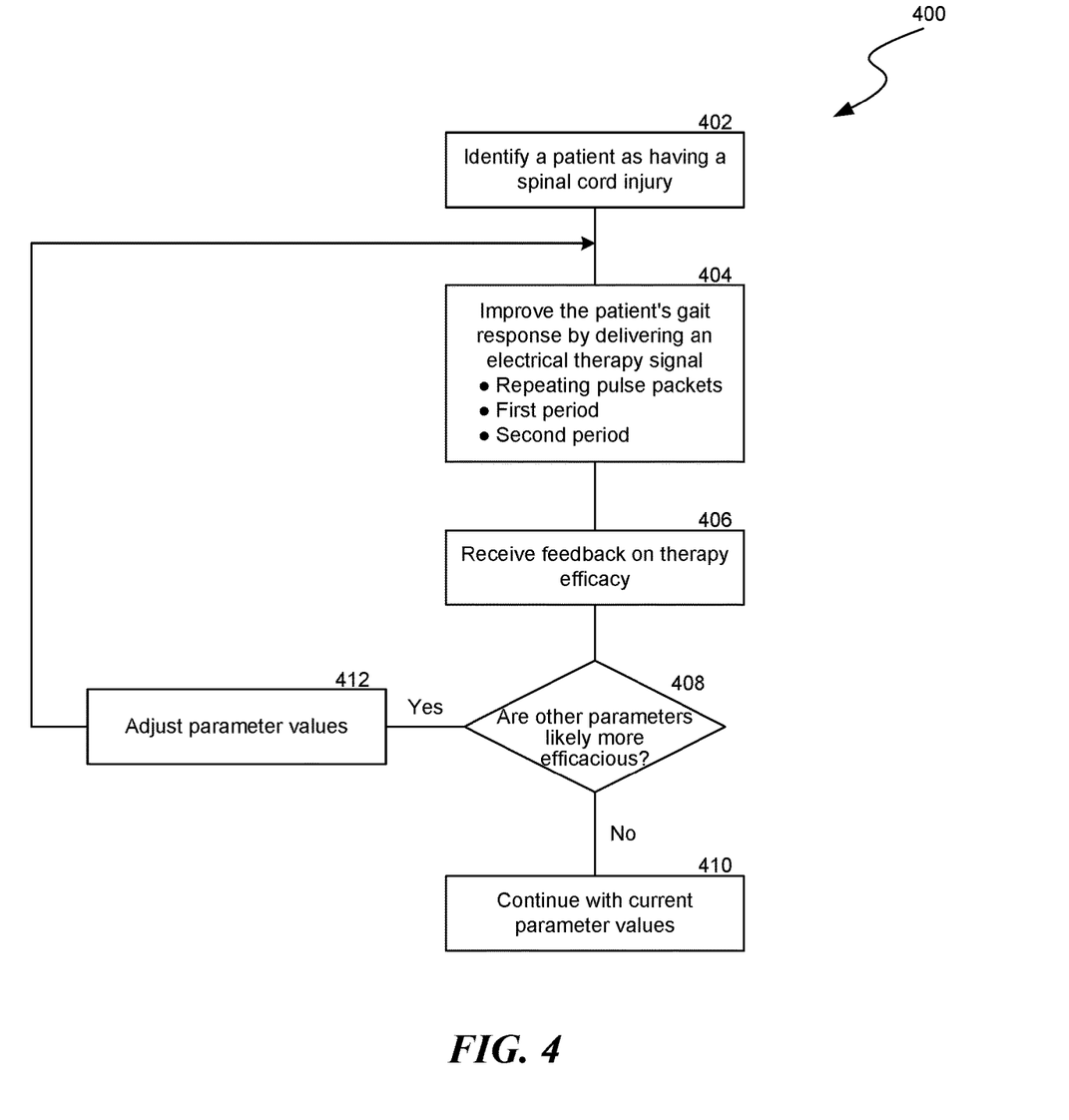
FIG. 4 is a flow diagram illustrating representative methods in accordance with embodiments of the present technology

FIG. 4 is a block diagram illustrating a representative method in accordance with embodiments of the present technology. The method 400 can include identifying a patient as having a spinal cord injury (block 402). At block 404, the method can include improving the patients gait response by delivering an electrical therapy signal. The electrical therapy signal includes pulse packets that each include a first period and a second period. As discussed above, the first period can include pulses having a selected pulse width, frequency, and amplitude, and the second period can include no pulses, or pulses delivered at any of a frequency higher than that of the first pulses, an amplitude lower than that of the first pulses, and a pulse width shorter than that of the first pulses. The electrical signal can be delivered simultaneously with the patient undergoing a selected motor activity, e.g., ambulation for a patient having a gait-related dysfunction. In a further example, the patient can receive two electrical signals: one while undergoing the selected motor activity and one while not undergoing the selected motor activity. The second electrical signal can include the second pulses, but not the first pulses.

At block 406, the method 400 includes receiving feedback on the efficacy of the therapy. At block 408, the method includes determining whether other parameter values are likely to be more efficacious that those in current use. If not, then the process 400 continues at block 410 with delivering therapy in accordance with the current parameter values. If at block 408, it is determined that other parameter values are likely to be more efficacious, than at block 412, the parameter values are adjusted, and the process returns to block 404.

As discussed above, one feature of embodiments of the present technology includes the ability to address disturbances in a patient's gait, resulting from a spinal cord injury. An advantage of this feature is that it can allow the patient to improve his or her gait, on a continuous or as-needed basis. In a further aspect of embodiments of the present technology, the patient can receive, in addition to therapy specifically directed at improving the patient's gait, therapy directed to reducing the patient's pain. Portions of the therapy signal can be delivered in the form of packets, with periods specifically selected to address patient gait (and/or other disfunctions) and/or patient pain.

From the foregoing, it will be appreciated that specific embodiments of the disclosed technology have been described herein for purposes of illustration, but that various modifications may be made without deviating from the technology. For example, the first and second pulses can be delivered at combinations of parameter values within the foregoing ranges that are not expressly disclosed herein. Certain aspects of the technology described in the context of particular embodiments may be combined or eliminated in other embodiments. For example, patients may selectively receive the first pulses only when undergoing ambulatory activity (and/or other motor activity), and/or may selectively receive the second pulses only when experiencing chronic pain. In some embodiments, the foregoing techniques can be used to address patient deficits other that gait-related deficits. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

To the extent any materials incorporated herein by reference conflict with the present disclosure, the present disclosure controls.

5.0 Representative Examples

The following examples are provided to further illustrate embodiments of the present technology and are not to be interpreted as limiting the scope of the present technology. To the extent that certain embodiments or features thereof are mentioned, it is merely for purposes of illustration and, unless otherwise specified, is not intended to limit the present technology. It will be understood that many variations can be made in the procedures herein described while still remaining within the bounds of the present technology. Such variations are intended to be included within the scope of the presently disclosed technology.

1. A patient treatment method, comprising:
   identifying a patient as having a spinal cord injury; and
   improving the patient's gait response by delivering, from an epidural location at the patient's spinal cord region, an electrical signal that includes repeating pulse packets delivered at a packet frequency of 33 Hz, wherein individual pulse packets include:
   first pulses delivered at a first frequency of 3 kHz and a pulse width of 140 microseconds for a first period of 3 milliseconds; followed by
   second pulses deliver at a second frequency of 10 kHz and a pulse width of 30 microseconds, for a second period of 27 milliseconds.
2. The method of example 1 wherein the first pulses are delivered at an amplitude of from 0.1 mA to 20 mA.
3. The method of example 1 wherein the first pulses are delivered at an amplitude of 5 mA.
4. The method of example 1 wherein the second pulses are delivered at an amplitude of from 0.01 mA to 20 mA, and less than an amplitude of the first pulses.
5. The method of example 1 wherein the epidural location is at a vertebral level of T8-T12.
6. The method of example 1 wherein the first pulses are square, symmetric, biphasic, pulses.
7. The method of example 1 wherein the second pulses are square, symmetric, biphasic, pulses.
8. The method of example 1 wherein the first and second pulses are delivered to a dorsal region of the patient's spinal cord.
9. The method of example 1 wherein the electrical signal is selectively delivered while the patient is undergoing ambulatory motion.
10. The method of example 9 wherein the electrical signal is a first electrical signal, and wherein the method further comprises delivering a second electrical signal having the second pulses without the first pulses when the patient is not undergoing ambulatory motion.
11. A patient treatment method, comprising:
    in a patient having a spinal cord injury, improving the patient's gait response by delivering an electrical signal that includes repeating pulse packets delivered at a packet frequency of from 2 Hz to 200 Hz, wherein the electrical signal is delivered from an epidural location at the patient's spinal cord, and wherein individual pulse packets include:
    a first period during which pulses are delivered at a first frequency of from 1 kHz to 5 kHz and a first pulse width of from 80 microseconds to 400 microseconds and a first amplitude from 0.1 mA to 20 mA; followed by
    a second period during which pulses are (a) not delivered, or (b) delivered at a second frequency higher than the first frequency, and/or a second pulse width that is from 5 microseconds to 400 microseconds and is shorter than the first pulse width, and/or a second amplitude less than the first amplitude.

I claim:

1. A patient treatment method, comprising:
   identifying a patient as having a spinal cord injury; and
   improving the patient's gait response by delivering, from an epidural location at the patient's spinal cord region, an electrical signal that includes repeating pulse packets delivered at a packet frequency of 33 Hz, wherein individual pulse packets include:
   first pulses delivered at a first frequency of 3 kHz and a pulse width of 140 microseconds for a first period of 3 milliseconds; followed by
   second pulses deliver at a second frequency of 10 kHz and a pulse width of 30 microseconds, for a second period of 27 milliseconds.
2. The method of claim 1 wherein the first pulses are delivered at an amplitude of from 0.1 mA to 20 mA.
3. The method of claim 1 wherein the first pulses are delivered at an amplitude of 5 mA.
4. The method of claim 1 wherein the second pulses are delivered at an amplitude of from 0.01 mA to 20 mA, and less than an amplitude of the first pulses.
5. The method of claim 1 wherein the epidural location is at a vertebral level of T8-T12.
6. The method of claim 1 wherein the first pulses are square, symmetric, biphasic, pulses.
7. The method of claim 1 wherein the second pulses are square, symmetric, biphasic, pulses.
8. The method of claim 1 wherein the first and second pulses are delivered to a dorsal region of the patient's spinal cord.
9. The method of claim 1 wherein the electrical signal is selectively delivered while the patient is undergoing ambulatory motion.
10. The method of claim 9 wherein the electrical signal is a first electrical signal, and wherein the method further comprises delivering a second electrical signal having the second pulses without the first pulses when the patient is not undergoing ambulatory motion.

11. A patient treatment method, comprising:
in a patient having a spinal cord injury, improving the patient's gait response by delivering an electrical signal that includes repeating pulse packets delivered at a packet frequency of from 2 Hz to 200 Hz, wherein the electrical signal is delivered from an epidural location at the patient's spinal cord, and wherein individual pulse packets include:
- a first period during which pulses are delivered at a first frequency of from 1 kHz to 5 kHz and a first pulse width of from 80 microseconds to 400 microseconds and a first amplitude from 0.1 mA to 20 mA; followed by
- a second period during which pulses are (a) not delivered, or (b) delivered at a second frequency higher than the first frequency, and/or a second pulse width that is from 5 microseconds to 400 microseconds and is shorter than the first pulse width, and/or a second amplitude less than the first amplitude.

12. The method of claim 11 wherein, during the second period, the pulses are not delivered.

13. The method of claim 11 wherein, during the second period, the pulses are delivered at a second frequency higher than the first frequency.

14. The method of claim 11 wherein, during the second period, the pulses are delivered at a second pulse width shorter than the first pulse width.

15. The method of claim 11 wherein, during the second period, the pulses are delivered at a second amplitude less than the first amplitude.

16. A patient treatment system, comprising:
a signal generator;
an epidurally-implantable signal delivery device coupleable to the signal generator; and
a machine-readable medium having instructions that, when executed, direct the signal generator to generate an electrical signal that includes repeating pulse packets delivered at a packet frequency of from 2 Hz to 200 Hz and wherein individual pulse packets include:
- a first period during which pulses are delivered at a first frequency of from 1 kHz to 5 kHz and a first pulse width of from 80 microseconds to 400 microseconds and a first amplitude from 0.1 mA to 20 mA; followed by
- a second period during which pulses are (a) not delivered, or (b) delivered at a second frequency higher than the first frequency, and/or a second pulse width that is shorter than the first pulse width, and/or a second amplitude less than the first amplitude.

17. The system of claim 16 wherein the signal delivery device includes an elongated lead.

18. The system of claim 16 wherein the signal delivery device includes a paddle.

19. The system of claim 16 wherein the signal generator is implantable.

20. The system of claim 16 wherein a portion of the machine-readable medium is implantable and another portion is not implantable.

21. The system of claim 16 wherein:
the packet frequency is 33 Hz;
the first frequency is 3 kHz, the first pulse width is 140 microseconds, and the first period is 3 milliseconds; and
the second frequency is 10 kHz, the second pulse width is 30 microseconds, and the second period is 27 milliseconds.

* * * * *

UNITED STATES PATENT AND TRADEMARK OFFICE
CERTIFICATE OF CORRECTION

| | | |
|---|---|---|
| PATENT NO. | : 11,058,875 B1 | Page 1 of 1 |
| APPLICATION NO. | : 16/575797 | |
| DATED | : July 13, 2021 | |
| INVENTOR(S) | : Alex Zinner | |

It is certified that error appears in the above-identified patent and that said Letters Patent is hereby corrected as shown below:

In the Specification

Column 2, Lines 5-6, after "technology" insert -- . --.

Column 8, Line 60, delete "sensory perspective" and insert -- sensory perspective. --, therefor.

Signed and Sealed this
Tenth Day of May, 2022

Katherine Kelly Vidal
*Director of the United States Patent and Trademark Office*